(12) United States Patent
Speck et al.

(10) Patent No.: US 9,651,476 B2
(45) Date of Patent: May 16, 2017

(54) FLUID ANALYSIS BY OPTICAL SPECTROSCOPY WITH PHOTOACOUSTIC DETECTION

(71) Applicant: SCHLUMBERGER TECHNOLOGY CORPORATION, Sugar Land, TX (US)

(72) Inventors: Andrew J. Speck, Milton, MA (US); Andrew E. Pomerantz, Lexington, MA (US); Oliver C. Mullins, Ridgefield, CT (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 292 days.

(21) Appl. No.: 14/166,593

(22) Filed: Jan. 28, 2014

(65) Prior Publication Data

US 2015/0211983 A1    Jul. 30, 2015

(51) Int. Cl.
| | |
|---|---|
| *G01N 29/24* | (2006.01) |
| *G01N 29/032* | (2006.01) |
| *G01N 29/22* | (2006.01) |
| *G01N 21/00* | (2006.01) |
| *G01N 21/17* | (2006.01) |
| *G02F 1/39* | (2006.01) |

(52) U.S. Cl.
CPC .......... *G01N 21/1702* (2013.01); *G02F 1/39* (2013.01); *G01N 2201/0697* (2013.01); *G01N 2201/06113* (2013.01)

(58) Field of Classification Search
CPC .......... G01N 2021/1757; G01N 21/17; G01N 29/42; G01N 29/2418

USPC ................ 73/152.42, 24.01–24.015, 152.18
See application file for complete search history.

(56) References Cited

U.S. PATENT DOCUMENTS

| | | | |
|---|---|---|---|
| 4,512,197 | A | 4/1985 | Von Gutfeld et al. |
| 5,741,962 | A | 4/1998 | Birchak et al. |
| 6,672,163 | B2 | 1/2004 | Han et al. |
| 6,678,050 | B2 | 1/2004 | Pope et al. |
| 7,114,562 | B2 | 10/2006 | Fisseler et al. |
| 7,387,021 | B2 | 6/2008 | DiFoggio |

(Continued)

FOREIGN PATENT DOCUMENTS

| | | |
|---|---|---|
| WO | 2011011512 | 1/2011 |
| WO | 2011146068 | 11/2011 |

(Continued)

OTHER PUBLICATIONS

Speck et al., U.S. Appl. No. 14/166,623, filed Jan. 28, 2014: pp. 1-27.

(Continued)

*Primary Examiner* — Daniel S Larkin
*Assistant Examiner* — Anthony W Megna Fuentes

(57) ABSTRACT

A method for downhole fluid analysis by optical spectroscopy with photoacoustic detection includes positioning a photoacoustic system within a wellbore, applying a laser pulse to the fluid sample using the pulsed laser system, detecting, by the acoustic sensor, a time-resolved acoustic pulse generated by absorption of the laser pulse by the fluid sample, and determining a property of the fluid sample using the detected time resolved acoustic pulse. The photoacoustic system includes a pulsed laser system and an acoustic sensor.

23 Claims, 10 Drawing Sheets

(56) References Cited

U.S. PATENT DOCUMENTS

| | | | |
|---|---|---|---|
| 7,520,158 B2 | 4/2009 | DiFoggio | |
| 7,614,302 B2 | 11/2009 | DiFoggio et al. | |
| 7,644,993 B2 | 1/2010 | Kaminsky et al. | |
| 7,708,067 B2 | 5/2010 | Treviranus et al. | |
| 7,781,737 B2 | 8/2010 | Zhdaneev | |
| 7,821,635 B2 | 10/2010 | Pope et al. | |
| 7,828,058 B2 | 11/2010 | Fielder | |
| 7,835,003 B2 | 11/2010 | Jiang et al. | |
| 7,913,806 B2* | 3/2011 | Pabon | G01V 1/523 166/254.2 |
| 8,037,747 B2 | 10/2011 | DiFoggio | |
| 8,586,913 B2 | 11/2013 | Zhou et al. | |
| 2005/0160791 A1 | 7/2005 | Kung | |
| 2005/0223808 A1 | 10/2005 | Myers et al. | |
| 2005/0276285 A1* | 12/2005 | Huang | H01S 3/115 372/10 |
| 2006/0266109 A1 | 11/2006 | DiFoggio | |
| 2008/0247425 A1 | 10/2008 | Welford | |
| 2009/0288474 A1 | 11/2009 | Kalkman et al. | |
| 2010/0011836 A1 | 1/2010 | Kalkman et al. | |
| 2010/0147051 A1 | 6/2010 | Tobias | |
| 2010/0195679 A1 | 8/2010 | Kroupa et al. | |
| 2011/0016962 A1 | 1/2011 | DiFoggio | |
| 2011/0023594 A1 | 2/2011 | Pelletier et al. | |
| 2011/0191027 A1* | 8/2011 | Pfutzner | E21B 47/10 702/6 |
| 2012/0055232 A1 | 3/2012 | Thorson | |
| 2012/0167693 A1* | 7/2012 | Asao | A61B 5/0059 73/655 |
| 2012/0269214 A1* | 10/2012 | Li | H01S 3/0627 372/11 |
| 2013/0056626 A1 | 3/2013 | Shen et al. | |
| 2013/0145813 A1* | 6/2013 | Pleban | G01N 21/25 73/1.06 |

FOREIGN PATENT DOCUMENTS

| | | |
|---|---|---|
| WO | 2012005725 | 1/2012 |
| WO | 2012030418 A1 | 3/2012 |
| WO | 2013090108 | 6/2013 |

OTHER PUBLICATIONS

Andrews et al., "Revealing Reservoir Secrets Through Asphaltene Science," Oilfield Review, Winter 2012/2013: pp. 14-25.
Chaudhuri et al., "An Algorithm for Determining Volume Fractions in Two-Phase Liquid Flows by Measuring Sound Speed," Journal of Fluids Engineering, vol. 134(10): pp. 101301-1-101301-7.
Fujisawa et al., "Development and Applications of Ruggedized VIS/NIR Spectrometer System for Oilfield Wellbores," Photonic Sensors, 2013, vol. 3(4): pp. 289-294.
"Insitu Fluid Analyzer," Schlumberger Brochure, 2008: pp. 1-8.
Kharrat et al., "Asphaltene Content Measurement Using an Optical Spectroscopy Technique," energy & fuels, 2013, vol. 27: pp. 2452-2457.
McCain et al., "Coefficients of Isothermal Compressibility of Reservoir Oils," Petroleum Reservoir Fluid Property, PennWell Corporation: Tulsa, 2011: pp. 54-73.
Michaelian et al., "Photoacoustic FT-i.r. spectra of separated western Canadian coal macerals: Analysis of the CH stretching region by curve-fitting and deconvolution," Fuel, Oct. 1990, vol. +-: pp. 1271-1275.
Mullins, "Asphaltenes and equilibrium fluid distributions," "Compartments" and "Oil chemistry," The Physics of Reservoir Fluids: Discovery Through Downhole Fluid Analysis, Schlumberger: Sugar Land, 2008: pp. 15-24 and pp. 43-46 and pp. 82-100.
Park et al., "Photoacoustic effect in strongly absorbing fluids," Ultrasonics, Jan. 1991, vol. 29: pp. 63-67.
Ruiz-Morales et al., "Polycyclic Aromatic Hydrocarbons of Asphaltenes Analyzed by Molecular Orbital Calculations with Optical Spectroscopy," Energy & Fuels, 2007, vol. 21: pp. 256-265.
Zhao et al., "Multiparameter measurement of absorbing liquid by time-resolved photoacoustics," Applied Optics, Mar. 2012, vol. 51(8): pp. 1061-1066.
International Search Report & Written Opinion for corresponding PCT Serial No. PCT/US2014/069770, dated Mar. 31, 2015, 16 pp.

* cited by examiner

FLUID ANALYSIS BY OPTICAL SPECTROSCOPY WITH PHOTOACOUSTIC DETECTION

CROSS-REFERENCE TO RELATED APPLICATION

This application is related to U.S. patent application Ser. No. 14/166,623, filed on Jan. 28, 2014 and entitled "Fluidic Speed of Sound Measurement Using Photoacoustics," which is hereby incorporated by reference in its entirety.

BACKGROUND

Downhole fluid analysis may be performed to estimate the level of contamination in downhole fluid samples and to provide information on the composition and properties of formation fluids. One example of a technique used for downhole fluid analysis is optical spectroscopy. In optical spectroscopy, the fluid sample of interest is illuminated with photons (electromagnetic waves) and the fluid may absorb photons having one or more different energies (wavelengths). The particular energy absorbed is related to the chemical composition and physical nature of the atoms and molecules making up the fluid and thus, the optical absorption/transmission measured as a function of energy (wavelength) of the photon, referred to herein as an optical absorption/transmission spectrum, may be used to estimate the chemical composition of the fluid.

Optical spectra are traditionally recorded in transmission mode. In transmission mode, photons are directed through the fluid sample towards a photon detector, and the number of photons transmitted through the sample is recorded. Photons that do not pass through the sample are assumed to have been absorbed by the sample. However, a second process can occur that may also prevent photons from passing through the sample and reaching the detector. This second process is referred to herein as scattering. As opposed to absorption, scattering of photons may not necessarily provide the desired information regarding the chemical composition of the sample or may serve to greatly complicate the interpretation of any measured optical spectrum.

In some conventional oil and gas reservoirs, scattering may often be ignored. However, scattering in some oils, such as heavy oils, cannot be ignored and in fact typically dominates over absorption. As a result, the absorption spectrum of heavy oils cannot be measured by traditional optical spectroscopy in transmission mode.

SUMMARY

Illustrative embodiments of the present disclosure are directed to a method for downhole fluid analysis by optical spectroscopy with photoacoustic detection. The method includes positioning a photoacoustic system within a wellbore, applying a laser pulse to the fluid sample using a pulsed laser system, detecting, by an acoustic sensor, a time-resolved acoustic pulse generated by absorption of the laser pulse by the fluid sample, and determining a property of the fluid sample using the detected time resolved acoustic pulse.

Also, various embodiments of the present disclosure are directed to a wellbore tool for downhole fluid analysis by optical spectroscopy with photoacoustic detection. The wellbore tool includes a photoacoustic spectroscopy system for analyzing a fluid sample. The photoacoustic spectroscopy system includes a laser system that is configured to generate laser pulses having a tunable wavelength, a window disposed between the fluid sample and the laser system and configured to transmit the laser pulses to the fluid sample. An acoustic sensor is configured to receive acoustic pulses that are generated in response to absorption of the laser pulses by the fluid sample.

Also, various embodiments of the present disclosure are directed to a method for analyzing a fluid sample. The method includes applying a laser pulse to the fluid sample using a laser system, wherein less than 37% of light from the laser pulse is transmitted through the fluid sample. The method further includes detecting, using an acoustic sensor, a time-resolved acoustic pulse generated by absorption of the laser pulse by the fluid sample and determining a property of the fluid sample using the detected time resolved acoustic pulse.

DETAILED DESCRIPTION

Illustrative embodiments of the present disclosure are directed to systems and methods for optical spectroscopy with photoacoustic (PA) detection of fluid properties. Photoacoustic detection is a detection scheme that is sensitive to absorption but largely insensitive to scattering. Thus, in various embodiments, photoacoustic detection may be used to record optical spectra of heavy oils or any other fluid where a non-negligible amount of scattering may be present, such as in emulsions and/or other highly scattering media (e.g., fluids contaminated with fine particles). In addition, photoacoustic detection may allow for a significantly higher dynamic range of absorbing samples as compared to traditional optical absorption spectroscopy. This increased dynamic range is due to the fact that the photoacoustic detection signal increases with higher absorption. For example, in some embodiments, photoacoustic spectroscopy may measure fluids with an absorption coefficient that is greater than 1000 $cm^{-1}$.

The detection system described herein is largely wavelength independent because the detected signal is acoustic rather than electromagnetic. This is to be contrasted with techniques that employ photon (electromagnetic wave) detectors, such as photodiodes, that normally have energy (wavelength) dependent sensitivities. Systems that employ photodiodes for broadband electromagnetic detection may therefore require several different types of detectors, each for detecting photons within a different energy (wavelength) range and furthermore, there may be some energy (wavelength) ranges that cannot be detected at all. In contrast, the photoacoustic detection system described herein allows for the same acoustic detector to be used across a wide wavelength range (e.g., from the ultraviolet to the mid-infrared range and beyond). Accordingly, a whole suite of different measurements (e.g., from crude oil color to the fingerprints of functional groups in the mid-infrared range) may be made without the need for complex detection hardware that combines a number of wavelength specific detectors.

Furthermore, as compared to photodiodes that are used for optical detectors, a photoacoustic sensor based measurement may be used at much higher temperatures. While a photodiode's shunt resistance significantly degrades with temperature due to the small bandgaps required for near-infrared sensing, various embodiments of the photoacoustic detection system described herein use one or more acoustic detectors (e.g., piezoelectric microphones, or the like) that operate at the elevated temperatures typical of wellbore environments (e.g., temperatures greater than 100° C., 150° C., or 200° C.).

Figure 1:
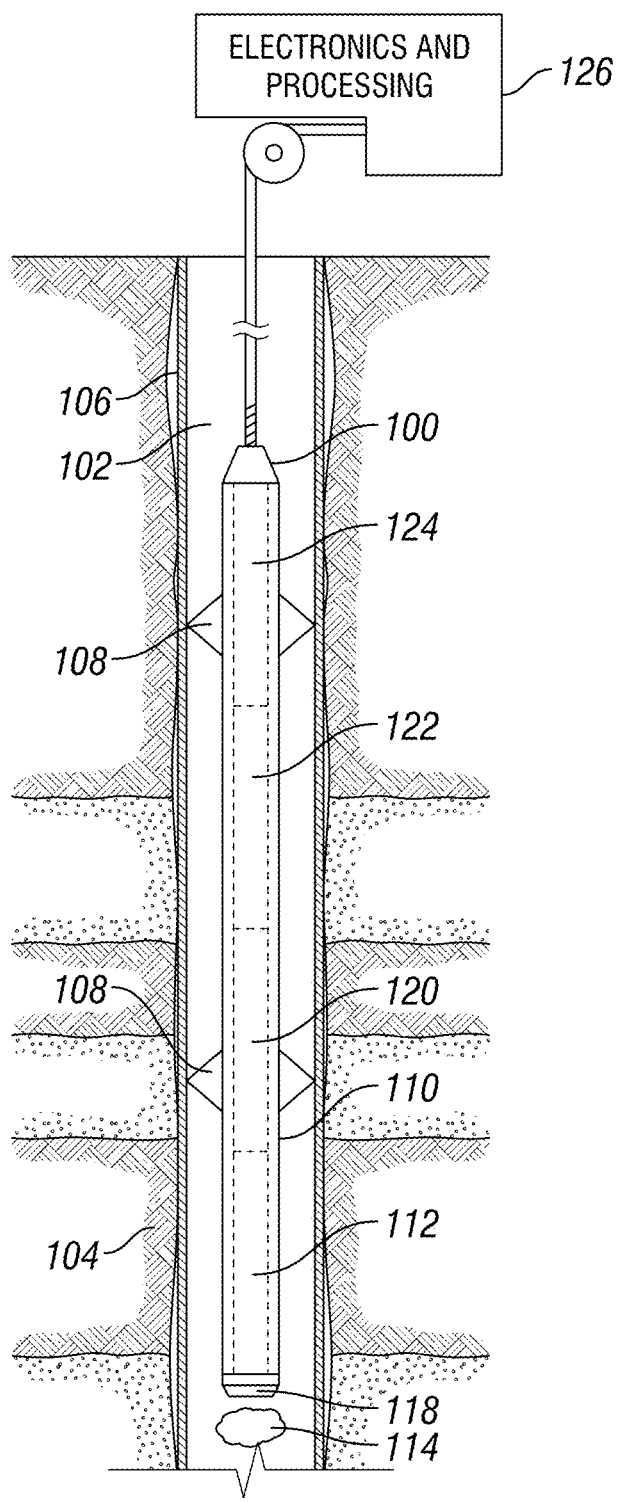
FIG. 1 shows a wellbore tool for fluid analysis by optical spectroscopy with photoacoustic detection in accordance with one or more embodiments.

Illustrative embodiments of the present disclosure are directed to oil field and gas field wellbore applications, such as production logging and wireline logging applications. FIG. 1 shows an example of a wellbore tool 100 that incorporates an embodiment of a photoacoustic detection system as described herein. In this case, the wellbore tool 100 is a production logging tool that is disposed within a wellbore 102 that traverses an earth formation 104. The wellbore 102 includes a casing 106 and the production logging tool 100 is lowered into the casing 106 via a wireline cable and may be centered within the casing using a set of centralizers 108. During production logging, formation fluid (e.g., formation liquid and/or formation gas) is extracted from different pay zones of the earth formation 104. As the formation fluid flows to the surface, the production logging tool 100 may be used to monitor the characteristics of the fluid (e.g., composition). As shown in FIG. 1, the production logging tool 100 includes a housing 110 that houses a plurality of system s 112, 120, 122, and 124. At one end, the housing 110 includes a photoacoustic system 112 for performing optical spectroscopy with photoacoustic detection on a sample of the formation fluid 114. The photoacoustic system 112 includes optics, at least one acoustic detector, and a pulsed light source, such as a pulsed laser, that correspond with the embodiments described, for example, in International Patent Application Publication No. WO 2013/090108, published on Jun. 20, 2013, which is incorporated by reference herein in its entirety. The laser generates light that is used to analyze the sample of formation fluid 114 using optical spectroscopy with photoacoustic detection. The light that scatters back from the sample may also be detected by a photodetector or may be ignored. Optics may be used to communicate the laser light to and from the formation fluid 114. In accordance with one or more embodiments, the photoacoustic system 112 may be in optical communication with the formation fluid sample via a window 118. In this manner, the sample of formation fluid 114 adjacent the window 118 may be analyzed by the photoacoustic system 112. In this case, the window 118 is located at the lower end of the tool and includes an acoustic sensor attached thereto for detecting the photoacoustic signal. In additional or alternative embodiments, the window and acoustic detector are located on a sidewall of the housing 110. In yet another embodiment, a window and acoustic detector may be located at the end of the housing 110 and one or more windows and acoustic detectors may be located on the side of the housing 110.

The production logging tool 100 also includes several other systems that support the photoacoustic system 112. For example, the production logging tool 100 includes a power system 120 to provide power to the various components of the system (e.g., the laser and the acoustic detector). Also, the production logging tool 100 may include an amplification system 122 to amplify an electrical signal that is output from the photoacoustic system 112. This electrical signal may be representative of a detected acoustic pulse that is generated by laser light that is absorbed by the fluid sample. Furthermore, the production logging tool may include a telemetry system 124 to provide communication between the production logging tool and surface electronics and processing systems 126. In one example, the telemetry system 124 communicates the electrical signal from the photoacoustic system 112 to the surface.

Figure 2:
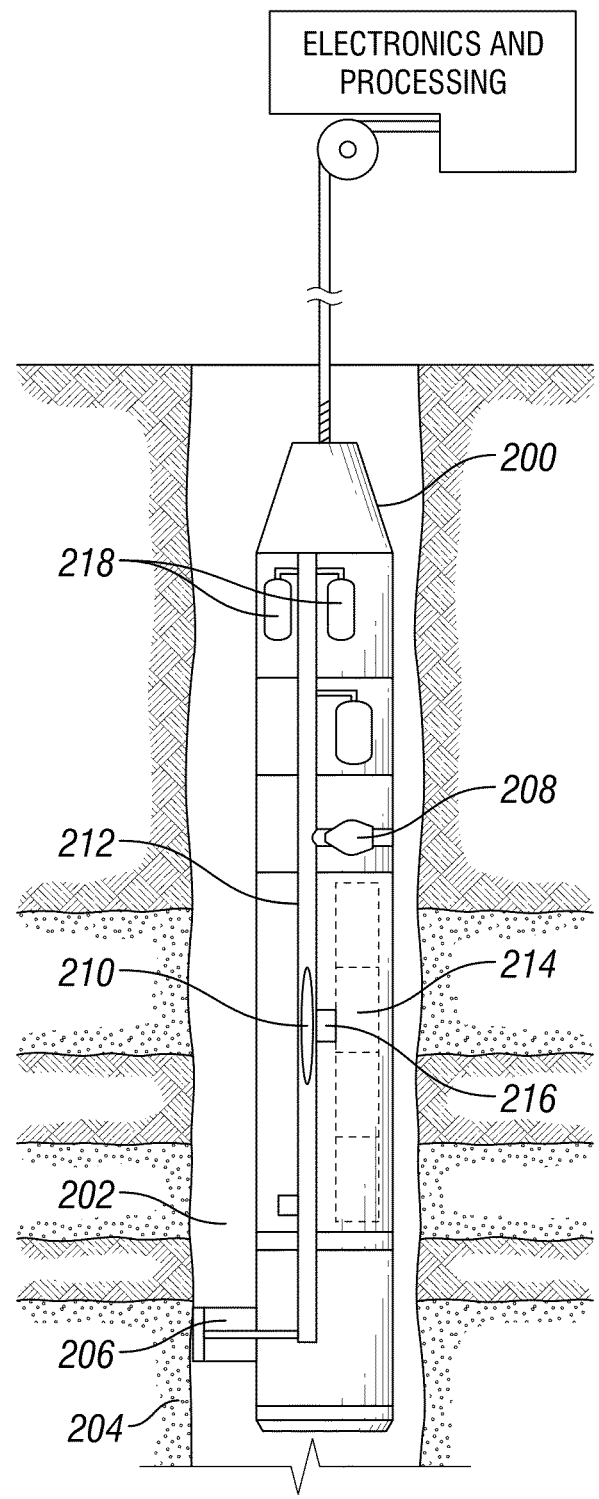
FIG. 2 shows a wellbore tool for fluid analysis by optical spectroscopy with photoacoustic detection in accordance with one or more embodiments.

FIG. 2 shows another wellbore tool 200 that incorporates an embodiment of a system for optical spectroscopy with photoacoustic detection in accordance with one or more embodiments. The downhole tool 200 is a wireline tool and is suspended within a wellbore 202 that traverses an earth formation 204. The tool 200 may be suspended within the wellbore using a multiconductor cable that is spooled on a winch at the surface. In contrast to the embodiment of FIG. 1, in which the formation fluid sample is analyzed outside the downhole tool 100, in this embodiment, the wireline tool 200 draws a fluid sample (e.g., formation fluid or wellbore fluid) into the tool and analyzes the sample within the tool. In accordance with one or more embodiments, the wireline tool 200 includes a formation tester 206 having a selectively extendable probe assembly. The selectively extendable probe assembly is configured to fluidly couple to an adjacent formation 204 and to draw fluid samples from the formation. A pump 208 is used to pass a fluid sample 210 through the probe assembly and into a flow line 212 within the tool 200.

The wireline tool 200 also includes a photoacoustic system 214 for performing optical spectroscopy with photoacoustic detection on the fluid sample 210 within the flow line 212. The photoacoustic system 214 includes a laser, optics and at least one acoustic detector that correspond with the embodiments described herein. The photoacoustic system 214 is in optical communication with the fluid sample 210 within the flow line 212 via a window 216. Accordingly, the fluid sample 210 within the flow line 212 may be analyzed by the photoacoustic system 214. Once the fluid sample 210 is analyzed, the sample can be expelled through a port (not shown) or the sample may be sent to one or more fluid collecting chambers 218.

Various embodiments of the present disclosure are not limited to the production logging tool 100 and the wireline tool 200 shown in FIGS. 1 and 2. For example, in some embodiments, a wireline tool may include a window and a photoacoustic system for analyzing fluid samples within the wellbore and outside the tool, in a similar manner to the production logging tool 100 of FIG. 1. One or more embodiments of the present disclosure may also be used in drilling applications, such as logging-while-drilling (LWD) systems or measurement-while-drilling (MWD) systems. In one particular embodiment, the LWD system includes a sampling-while-drilling system (e.g., the sampling-while-drilling system is part of an LWD tool suite). In the sampling-while-drilling system, a fluid sample may be drawn into the system from the formation and analyzed within the tool, in a similar manner to the wireline tool 200 of FIG. 2. Further details of one example of sampling-while-drilling systems are provided in U.S. Pat. No. 7,114,562, issued on Oct. 3, 2006 and entitled "Apparatus and Method for Acquiring Information while Drilling." Furthermore, the tools described above can be used with any suitable means of conveyance, such as drill pipe, armored cable, or coiled tubing.

Figure 3A:
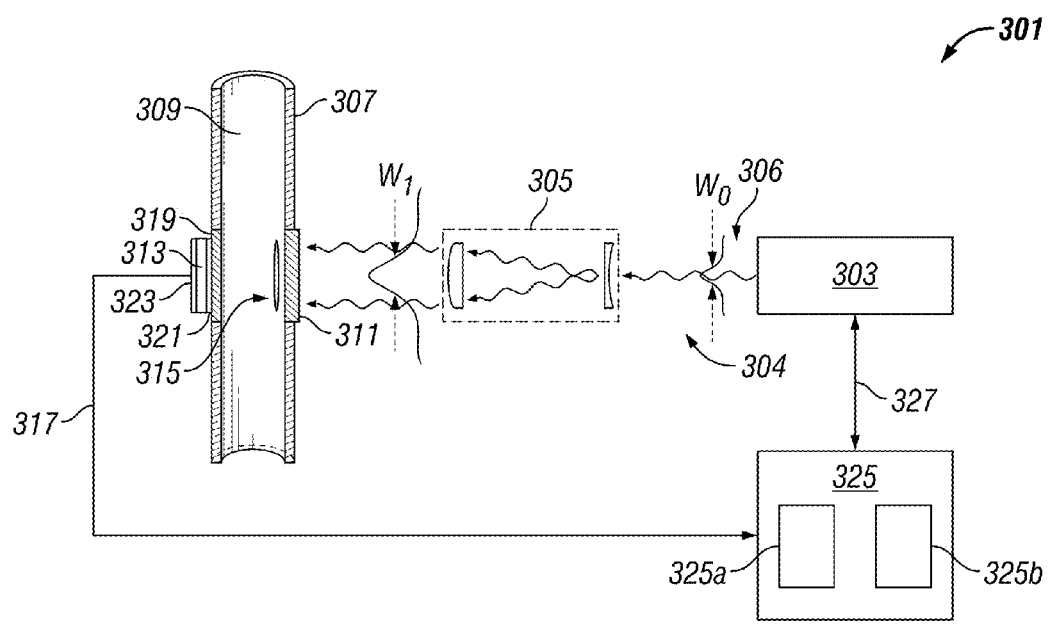
FIGS. 3A-3B show photoacoustic systems for wellbore tools in accordance with one or more embodiments.
Figure 3B:
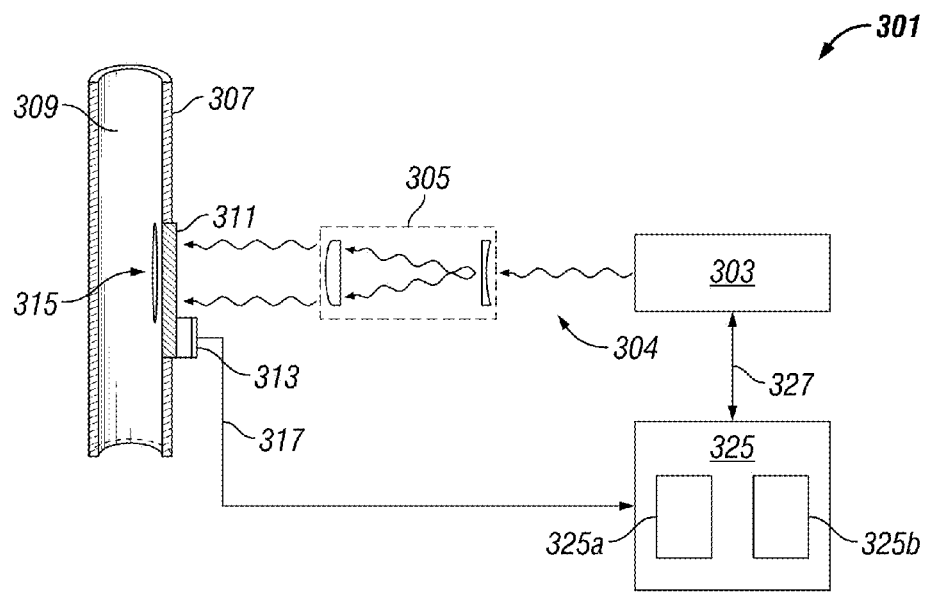

FIGS. 3A-3B show illustrative examples of photoacoustic systems 301 in accordance with one or more embodiments. FIG. 3A shows an example of a flow line based photoacoustic system 301 that employs a pulsed laser system 303 for conducting optical spectroscopy with photoacoustic detection on a fluid of interest. In accordance with one or more embodiments, the photoacoustic system 301 includes processing system 325, a pulsed laser system 303, a beam shaper 305, and a flow line 307 that serves as a fluid vessel for containing the fluid 309 under test. The flow line 307 further includes a window 311 and an acoustic sensor 313. As shown in the figures, the window 311 is disposed between the fluid 309 and the laser system 303. The pulsed laser system 303 emits one or more laser pulses 304 each having a wavelength $\lambda_{pulse}$ and a beam diameter $w_0$. For example, in accordance with one or more embodiments, the wavelength $\lambda_{pulse}$ of the laser pulse is about 1390 nm, which leads to an absorption coefficient in water of 10 cm$^{-1}$. The laser beam diameter w may be defined as the 1/e$^2$ diameter of the transverse spatial mode of the laser beam emitted from the laser system 303. For example, in the case of a transverse electromagnetic mode 0,0 (TEM$_{00}$), the output pulses of the laser system 303 may have an intensity distribution 306 that is Gaussian-shaped as measured along a direction that is perpendicular to the direction of pulse propagation (right-to-left direction in the FIG. 3A).

After generation by the laser system 303, the laser pulses 304 are directed to the beam shaper 305 that comprises a series of beam shaping optics that may be any collection of optics known in the art (e.g., lenses, mirrors, spatial filters, or the like). For example, the beam shaper 305 of FIG. 3A shows a lens pair that acts as a beam expanding telescope designed to expand the laser beam diameter from the laser output diameter $w_0$ to an expanded diameter $w_1$. In accordance with one or more embodiments, the optics used by the beam shaper 305 may be chosen to produce an expanded diameter $w_1$ that is much larger than a characteristic length scale d. For fluids characterized by an absorption coefficient that is large relative to the light path length (defined as the maximum distance the light may travel through the fluid, e.g., the width of the flow line), the characteristic length scale d may be the penetration depth of the laser pulse into the fluid under test, where the penetration depth is defined as the depth within the fluid at which the intensity of the laser pulse is reduced to 1/e of its initial value. However, if the absorption coefficient is very small relative to the light path length within the flow line, the characteristic length scale d may alternatively be the light path length. After passing through the beam shaper 305, the laser pulses 304 are transmitted through window 311 and are absorbed by fluid 309. In accordance with one or more embodiments, the material for window 311 may be chosen such that it is largely transparent at the laser wavelength $\lambda_{pulse}$ and further may also be largely transparent at any other wavelengths that may be used for the analysis (e.g., in the case where laser system 303 is a tunable laser for obtaining an absorption spectrum of the fluid). As used herein, the term spectrum refers to a photoacoustic measurement using laser pulses of several different wavelengths. Examples of tunable laser systems suitable in accordance with one or more embodiments are described below in reference to FIGS. 6A-6E.

Returning to FIG. 3A, each laser pulse of the laser pulses 304 is at least partially absorbed by the fluid thereby causing an excitation of the fluid's constituent molecules. The abrupt relaxation of the molecules in the fluid sample generates an acoustic impulse in a portion 315 of the fluid. The acoustic impulse propagates as an acoustic wave through the fluid 309 and is detected by the acoustic detector 313. In accordance with one or more embodiments, the acoustic detector 313 may be an ultrasonic transducer (e.g., that uses a piezoelectric element or the like). Furthermore, to minimize acoustic mismatches between the fluid and the detector, the acoustic detector 313 may be coupled to the fluid through a detector window 319 and/or through an acoustically matched layer 321, such as VITON™ rubber or polyether ether ketone (PEEK). Furthermore, in some embodiments, an absorbing backing material layer 323 that is acoustically matched to the detector window may be placed on the far side of the acoustic detector 313 to reduce ringing effects in the detector.

Figure 8A:
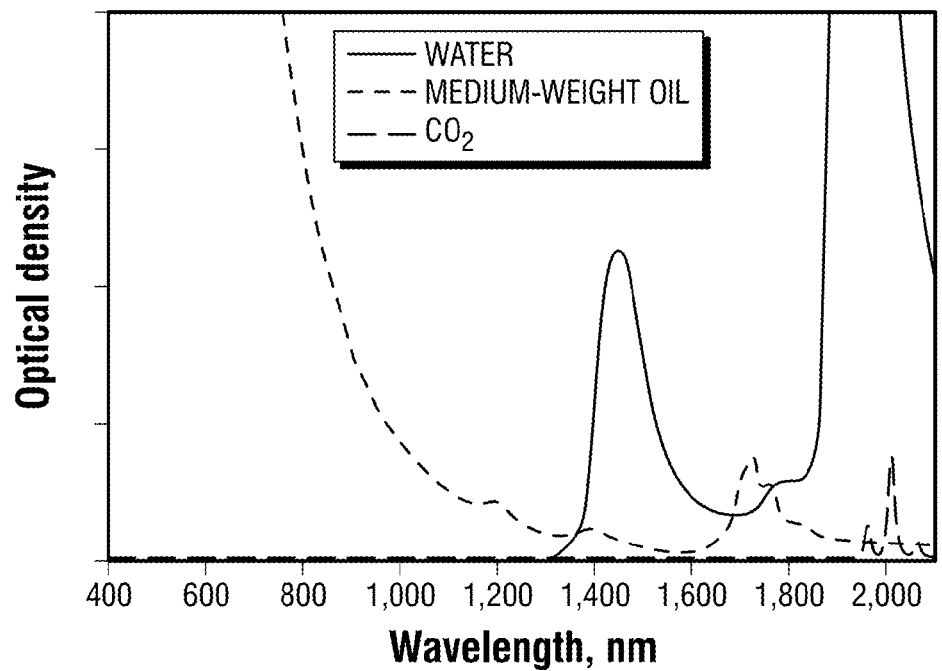
FIGS. 8A-8C show absorption spectra for several different fluids in accordance with one or more embodiments.
Figure 8B:
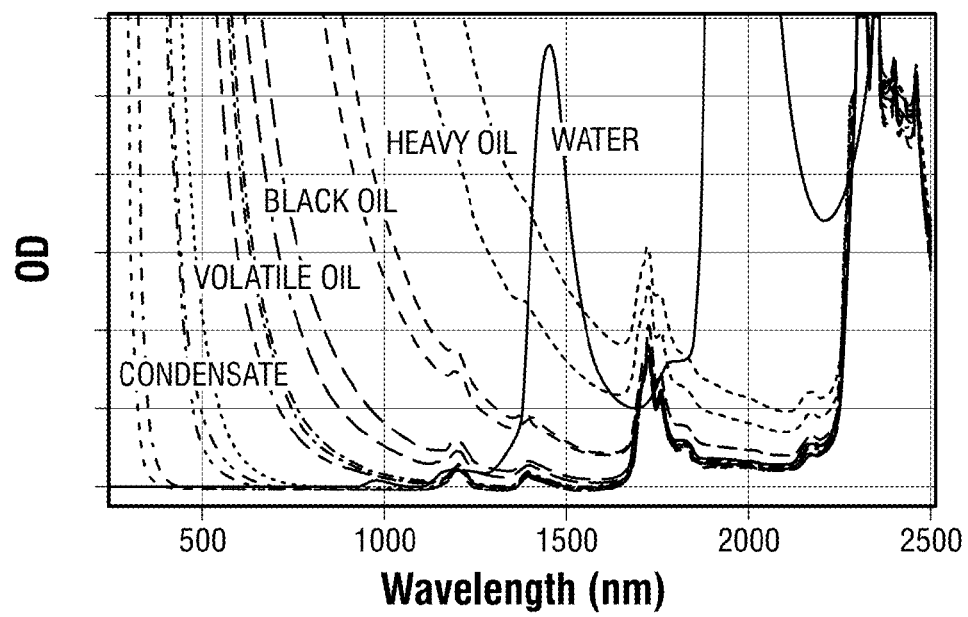
Figure 8C:
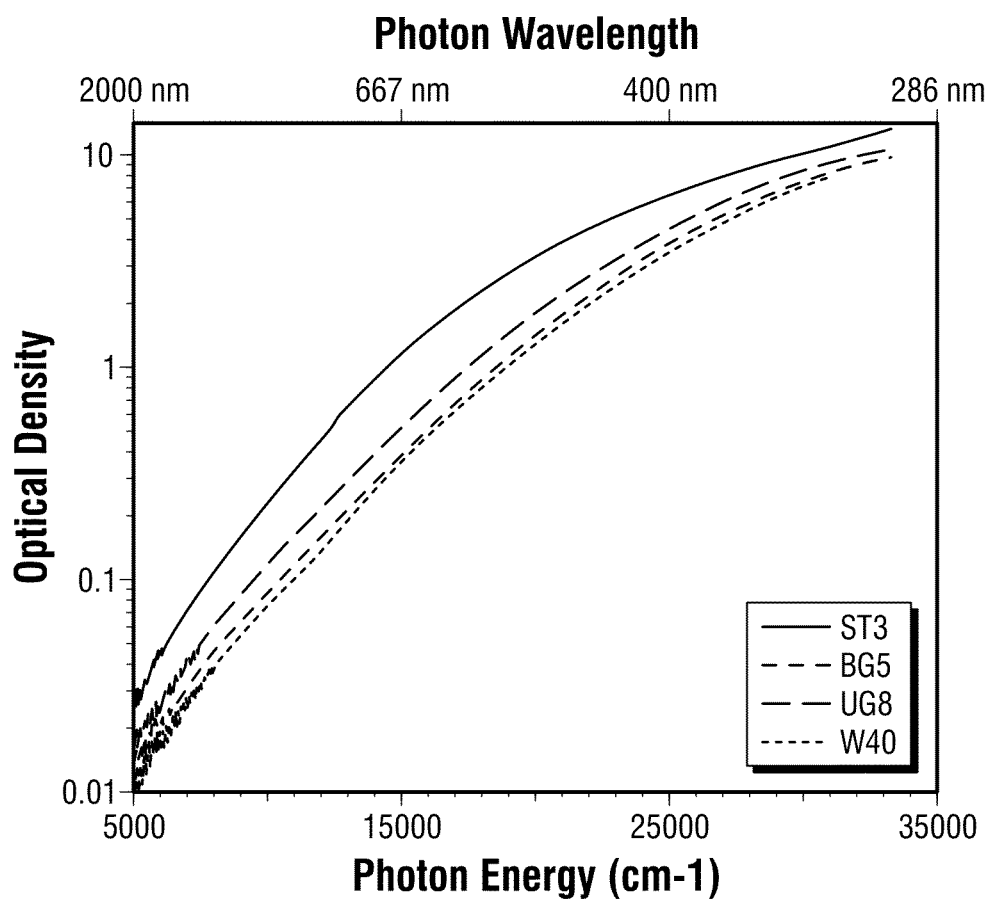

In some examples, the acoustic detector 313 may efficiently detect the acoustic wave and generate an electrical signal 317 that corresponds to the detected acoustic wave. The electrical signal 317 may then be routed or transmitted to processing system 325 for further processing. The processing system 325 includes one or more memories 325a and one or more processors 325b. Accordingly, the processing system 325 may store the electrical signal 317 in the form of acoustic pulse data and then further process the acoustic pulse data (e.g., to determine a property of the fluid under test such as an optical absorption coefficient). In some examples, an absorption spectrum may be determined by calculating one or more optical absorption coefficients based on acquired acoustic pulse data that was generated using one or more laser pulses having one or more different wavelengths. Further analysis may be done based on the absorption spectrum (e.g., one or more constituents of the fluid may be identified based on the shape of the absorption spectrum). In addition, other properties of the fluid may be determined using the measured value of the absorption coefficient at a particular wavelength, or over a particular wavelength range (e.g., a concentration of a fluid constituent may be determined). An example of the detected signal is described below in more detail in reference to FIG. 5B. Examples of absorption spectra for different fluid constituents are shown in FIGS. 8A-8C.

In some embodiments, the processing system 325 is configured to send/receive control signals to/from the laser system 303, respectively. For example, the processing system 325 may send control signals to the laser system to cause one or more pulses to be emitted from the laser system 303 in a precisely timed manner and may send control signals that control the particular wavelength at which the laser pulses. Thus, in accordance with one or more embodiments, programming stored on the memory in the form of computer readable instructions, when executed by the processor, cause the laser system 303 to emit several pulses at several different wavelengths. The acoustic data generated by each laser pulse at each wavelength may then be acquired and stored by the processing system and also may be processed to determine a property of the fluid (e.g., an absorption spectrum of the fluid). An example of how the acoustic data may be processed to obtain the absorption coefficient of the fluid is described in more detail below in reference to FIGS. 5A-5B.

FIG. 3B shows another example of a photoacoustic system 301 in accordance with one or more embodiments. This system is similar to the system described above in reference to FIG. 3A so repeated elements will not be described hereafter in detail. In the photoacoustic system 301 of FIG. 3B, the acoustic detector 313 is mounted to window 311 and thus is configured to detect acoustic waves generated by the absorption of the laser pulses 304 that travel back towards the window 311. Like the system described above in reference to FIG. 3A, the acoustic detector 313 may efficiently detect the acoustic wave and generate an electrical signal 317 that corresponds to the detected acoustic wave. The electrical signal 317 may then be routed or transmitted to processing system 325 for storage and further processing. The details of the processing system 325 are described above and thus will not be reproduced here.

As described above, the photoacoustic system 301 may be incorporated into a downhole fluid sampling tool and the flow line 307 may be configured to couple with the flow line of the tool. Thus, the photoacoustic system 301 may be used to characterize formation fluids or any other downhole fluid of interest (e.g., both wellbore fluid, drilling mud, and formation fluid) that may be sampled by the tool. Such a configuration was described above in reference to FIG. 2 and thus, the details will not be reproduced here.

Figure 4:
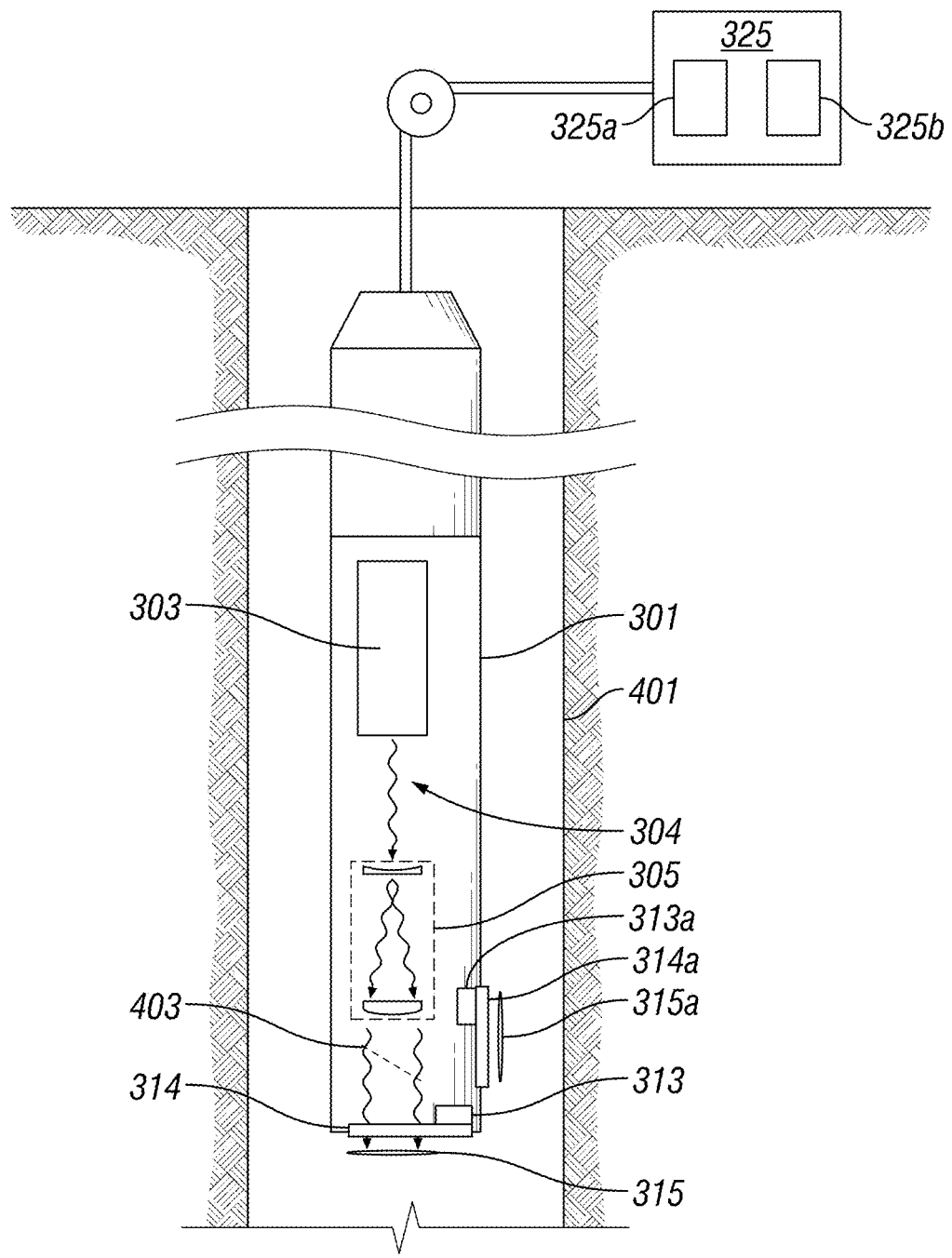
FIG. 4 shows another photoacoustic system for a wellbore tool in accordance with one or more embodiments.

FIG. 4 shows a photoacoustic system 301 having an arrangement that corresponds to that shown in FIG. 3A but arranged to be accommodated within a wellbore tool of the type shown in FIG. 1. In accordance with one or more embodiments, the photoacoustic system 301 may be a system that is designed to investigate wellbore fluids. Accordingly, the photoacoustic system 301 of FIG. 4 is shown inside wellbore 401. Window 314 is designed to isolate the interior of the wellbore 401 from the photoacoustic system 301. Accordingly, the window 314 is disposed between the laser system 303 and the wellbore fluid under test. Furthermore, in this example, the acoustic sensor 313 is disposed on the interior surface of the window 314, with the appropriate acoustic matching material, if necessary, and thus, is also isolated from the wellbore fluid. Also, shown in FIG. 4 is optical system 403 (e.g., one or more mirrors) that may be used to redirect the laser pulses 304 to a window 314a located on the side of the wellbore tool. Again, as described above, acoustic sensor 313a may be arranged on the inner surface of window 314a so as to detect backward-travelling acoustic waves that are generated from the absorption of the laser pulses 304 by the wellbore fluid portion 315a. In accordance with one or more embodiments, the photoacoustic system 301 may be deployed with one of or both of the arrangements described above without departing from the scope of the present disclosure. Like the systems described above in reference to FIGS. 3A-3B, the acoustic detector 313 may efficiently detect the acoustic wave and generate an electrical signal that corresponds to the detected acoustic wave. The electrical signal may then be routed or transmitted to processing system 325 for storage and further processing. The details of the processing system 325 are described above and therefore will not be reproduced here. While the system shown in FIG. 4 is shown as a wireline tool with processing system 325 shown as a surface unit, the processing system may be deployed within the tool itself without departing from the scope of the present disclosure. Furthermore, the several embodiments of the present disclosure are not limited to wireline tools but rather, the systems and methods disclosed herein may be employed within any type of wellbore tool.

Figure 5A:
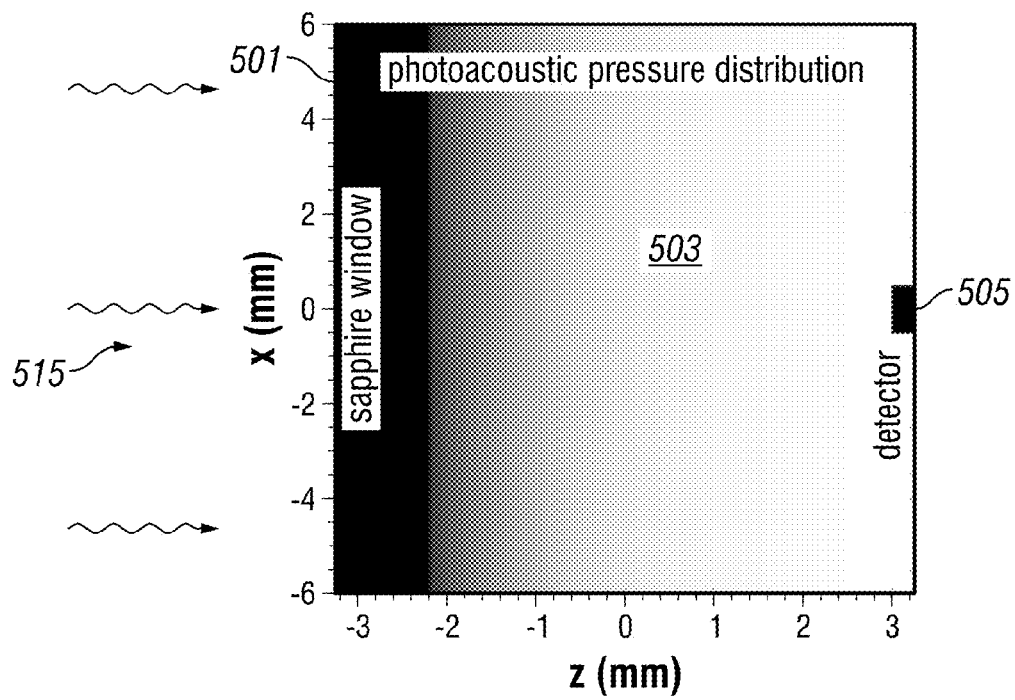
FIGS. 5A-5B show simulated photoacoustic data in accordance with one or more embodiments.
Figure 5B:
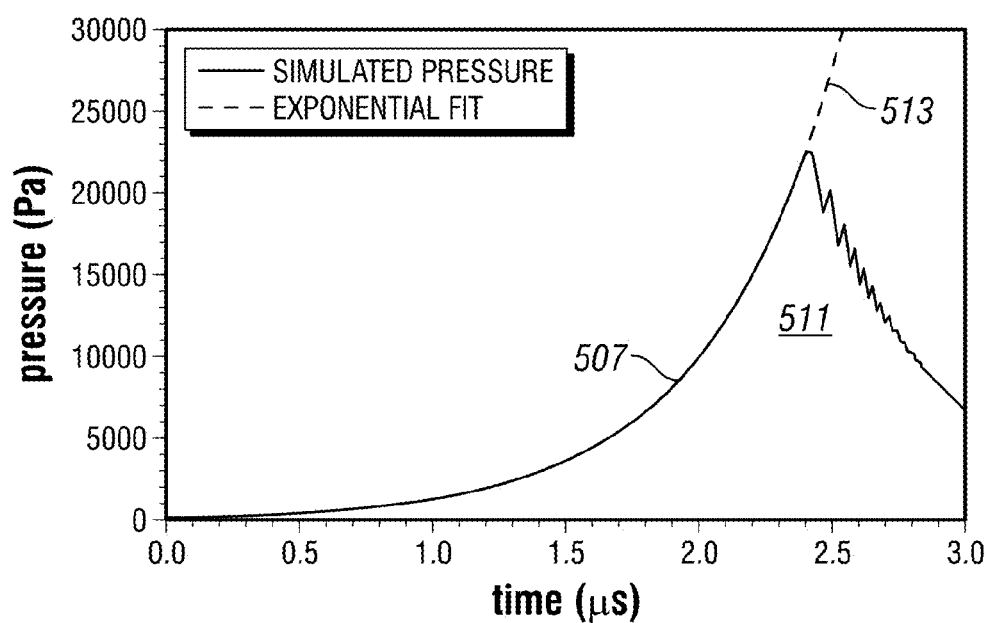

To further illustrate one example of the method of wellbore fluid analysis by optical spectroscopy with photoacoustic detection, FIGS. 5A-5B show a photoacoustic detection system and simulated test data numerically simulated using the system, respectively. In particular, the data shown in FIG. 5B represents time resolved acoustic data that may be detected by an acoustic system having the sensor arrangement as shown in FIG. 5A (e.g., corresponding to the flow line arrangement shown in FIGS. 2 and 3A). However, one of ordinary skill having the benefit of this disclosure will appreciate that the acoustic data for all the arrangements discussed herein may be similar to that shown in FIG. 5B.

The photoacoustic system shown in FIG. 5A includes a sapphire window 501 that is approximately 1 mm in thickness located at a z position of approximately 2.8 mm. An acoustic detector 505 is mounted approximately 6 mm from the sapphire window. A volume 503 between the window 501 and the detector 505 is filled with water. In some embodiments, the volume is the volume within a flow line. In this simulation, a laser pulse 515 having a wavelength of 1390 nm is incident on the window from the left. As described above, the optical absorption of the laser pulse by the fluid leads to an excitation of the fluid that manifests as a propagating pressure disturbance in the fluid, also referred to herein as a photoacoustic pressure distribution, or as a pressure wave. In FIG. 5A, the photoacoustic pressure distribution is shown as an intensity gradient in grayscale with a darker color indicating a higher pressure. After the photoacoustic pressure distribution is produced, it travels as a pressure wave 511 toward the acoustic detector 505. FIG. 5B shows a time resolved acoustic signal that is detected as the pressure wave 511 traverses the detector. As can be seen form FIG. 5B, in this example, the detector first detects an exponentially rising pressure 507 followed by an abrupt decrease in pressure as the photoacoustic pressure wave 511 passes the detector. In accordance with one or more embodiments, the exponential time constant of the exponential rising portion 507 of pressure wave 511 is directly proportional to the optical absorption coefficient α of the fluid (water, in this case). Thus, a measurement of the exponential rising portion 507 detected by the acoustic sensor 505 provides a measure of the optical absorption property of the fluid. While the above arrangement is configured to detect an acoustic wave that propagates parallel to the optical pulse, any number of different arrangements may be used without departing from the scope of the present disclosure. For example, the acoustic sensor may be positioned such that it measures an acoustic pulse that propagates in any direction relative to the laser beam propagation direction (e.g., perpendicular to, or even opposite to, the propagation direction of the optical pulse). Furthermore, in other embodiments, an array of acoustic sensors may be used to detect the acoustic pulse that propagates in a direction that is perpendicular to the propagation direction of the optical pulse.

In accordance with one or more embodiments, the pressure change Δp caused by the laser pulse absorption may be proportional to:

$$\Delta p \propto \frac{\beta c^2}{C_p} E_a \qquad (1)$$

where is β is the thermal expansion coefficient of the fluid, c is the speed of sound in the fluid, $C_p$ is the heat capacity of the fluid, and $E_a$ is the energy from the incoming laser beam that is absorbed by the fluid. Because the proportionality constant depends on sample constants, the actual measured signal may depend on specific fluid properties rather than just its absorptivity at a specific wavelength. Accordingly, ratio measurements may be used because the proportionality constant is wavelength independent. In other embodiments, calibration measurements may be made by injecting known heat pulses into the fluid sample and measuring the response to the heat pulses. In accordance with one or more embodiments, the calibration measurements may be performed by measuring the response of a step change in current applied to a wire within the sample or by utilizing a black body absorber placed on the side of the sample cell and illuminating the absorber with an incident laser pulse of known energy.

In accordance with one or more embodiments, a self-calibrated method may be used. In this method, the width of the input laser pulse may be widened such that its transverse dimensions are much larger than the depth of penetration of the laser energy and also the transverse dimensions of the acoustic detector. Under these conditions, a planar pressure wave front is generated that may be described using Beer's law, which models the amplitude of the pulse as function of propagation depth z within the fluid. Accordingly, the initial pressure distribution of the shock may be given by:

$$E_a(z) = -\frac{d}{dz}E_0 e^{-\alpha z} = E_0 \alpha e^{-\alpha z} \quad (2)$$

where $E_0$ is the initial energy of the laser pulse (before any of the pulse is absorbed by the fluid) and a is the absorption coefficient of the fluid. Inserting Eq. (2) into Eq. (1) leads to a formula for the pressure distribution as a function of the absorption coefficient $\alpha$.

$$\Delta p(z) \propto E_0 \alpha \frac{\beta c^2}{C_p} e^{-\alpha z} \quad (3)$$

Eq. (3) represents the pressure disturbance that travels at the speed of sound c towards the detector. Accordingly, the pressure at the detector located a distance from the input window can be written as:

$$\Delta p(t) \propto E_0 \alpha \frac{\beta c^2}{C_p} e^{-\alpha(z_0 - ct)} \quad (4)$$

Taking the logarithm of Eq. (4) reveals that the linear slope of the logarithm of the measured acoustic signal is only dependent on $\alpha$ and c:

$$\log(\Delta p(t)) \propto \alpha ct + (\log(S_m) - \alpha z_0) \quad (5)$$

$$\text{where } S_m = E_0 \alpha \frac{\beta c^2}{C_p}$$

is the (time independent) amplitude of the pressure disturbance. Thus, even if the speed of sound is not known, a measurement of the exponential rise 507 in the pressure disturbance 511 allows for a measurement of a quantity that is proportional to the absorption coefficient $\alpha$ because, as seen from Eq. (4) above, the time constant for the exponential rise is given by $\alpha c$. Stated another way, on a semi-log plot, the initial rise in the pressure is linear with time and, as shown in Eq. (5), has a slope of $\alpha c$. Thus, if c is uniform through the fluid and only a relative absorption measurement is desired, no additional calibration is needed; the measurement of the slope (or equivalently, a measurement of the time constant obtained by an exponential fit 513 to the measured pressure disturbance 511) yields the relative absorption. If an absolute measurement is desired, the speed of sound c may be measured for each pulse by measuring elapsed time from generation to detection of the acoustic pulse and dividing the known propagation distance (e.g., the distance between the acoustic window and the acoustic sensor) by the measured elapsed time, also accounting for the travel time through any acoustic matching layers, if desired. Further details of speed of sound measurements using the photoacoustic system are described in U.S. patent application Ser. No. 14/166,623, filed on Jan. 28, 2014 and entitled "Fluidic Speed of Sound Measurement Using Photo acoustics."

Figure 6A:
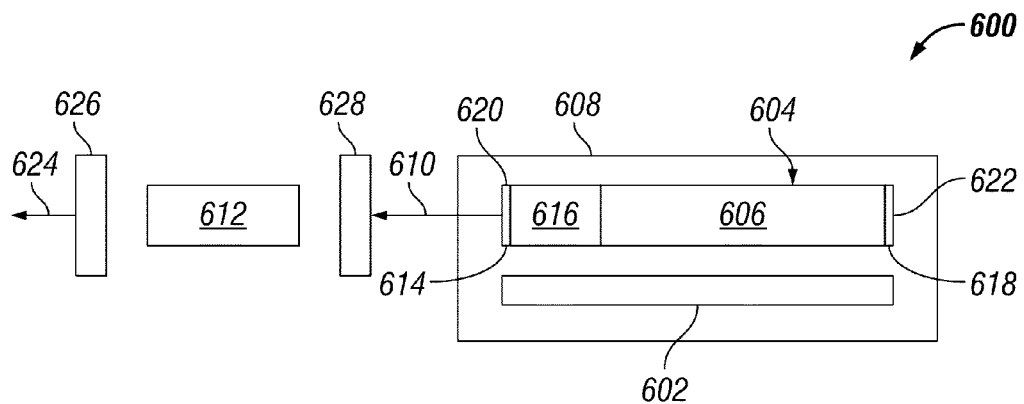
FIGS. 6A-6E show pulsed laser sources for a wellbore tool in accordance with one or more embodiments.
Figure 6B:
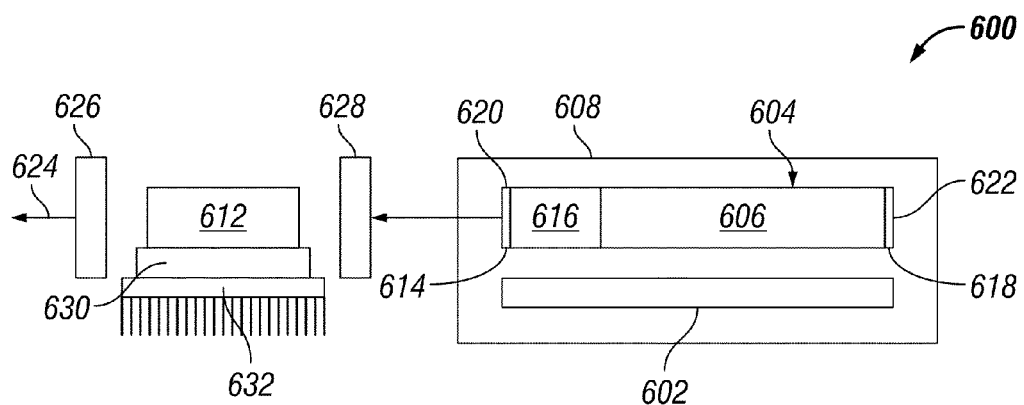
Figure 6C:
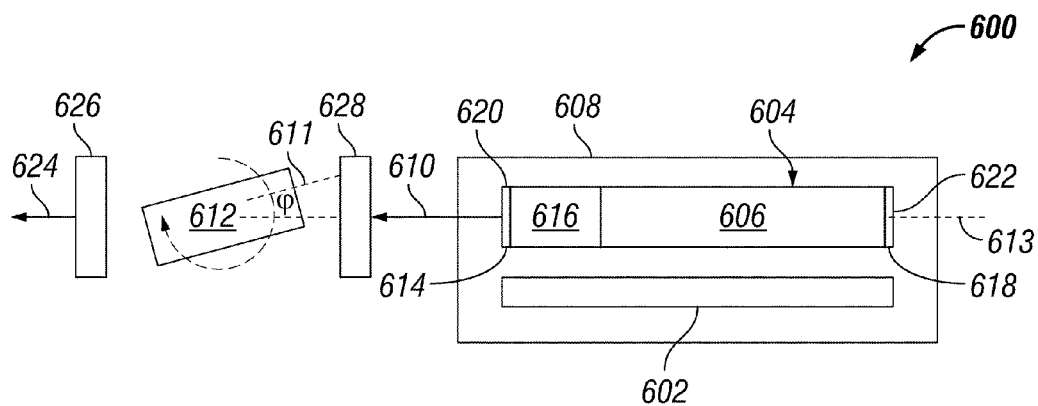

FIGS. 6A-6C show diagrams of pulsed laser sources 600 in accordance with one or more embodiments. These sources may be deployed as pulsed laser source 303 (e.g., as described above in reference to FIGS. 3-4 and may also be deployed within the wellbore tools described above in reference to FIGS. 1-2. As described in more detail below, the laser sources 600 use a monolithic Q-switched architecture that is adapted for stable wellbore use. In accordance with one or more embodiments, when the laser source 600 is exposed to temperatures between about room temperature and about 200° C., the laser source 600 outputs laser pulses having pulse energies (e.g., 8 mJ, 14 mJ, 22 mJ, etc.) substantially independent of the temperature. For example, in some embodiments, from about room temperature to about 200° C., the laser source 600 outputs laser pulses having pulse energies with a standard deviation within about 10 percent. Also, in accordance with one or more embodiments, the laser source 600 may output laser pulses even when subjected to shocks (e.g., a 500 g shock) and/or vibrations (e.g., a 0.5 $g^2/\sqrt{Hz}$ vibration).

The laser sources 600 of FIGS. 6A-6E include a pump source 602 such as, for example, a flash lamp, an arc lamp, an LED, a laser diode, and/or any other suitable pump source. The example pump source 602 may be adjacent a monolithic body 604 to transversely pump a solid state gain medium 606 of the monolithic body 604. In the illustrated examples, a reflective cavity 608 substantially encloses the monolithic body 604 and the pump source 602. In some examples, the reflective cavity 608 is defined by a substantially transparent (e.g., glass) cylinder at least partially covered by a diffuse reflector such as barium sulfate, Teflon, and/or any other suitable diffuse reflector. In other examples, the reflective cavity 608 may be an elliptical mirror.

The example monolithic body 604 of FIGS. 6A-6E includes a first reflector 614, a Q-switch 616, a solid state gain medium 606, and a second reflector 618. In the illustrated example, a first end of the Q-switch 616 is coupled to the solid state gain medium 606. In the illustrated example, the first reflector 614 is disposed on a first end 620 of the monolithic body 604 and the second reflector 618 is disposed on a second end 622 of the monolithic body 604. The first reflector 614 is coupled to the Q-switch 616, and the second reflector 618 is coupled to the solid state gain medium 606. In some examples, the first reflector 614 and/or the second reflector 618 are film coatings.

In the illustrated example, the first reflector 614 and the second reflector 618 provide an optical resonator (e.g., they reflect light in a closed path). In some examples, reflective surfaces of the first reflector 614 and the second reflector 618 are substantially parallel to each other. In other examples, the first reflector 614 and the second reflector 618 are curved. In some such examples, the first reflector 614 and the second reflector 618 are curved such that the first reflector 614 and the second reflector 618 are substantially confocal or substantially concentric.

In some examples, the solid state gain medium 606 is a material in a solid state such as, for example, a chromium doped beryllium aluminum oxide crystal ($Cr^{3+}:BeAl_2O_4$) ("alexandrite"), a neodymium-doped yttrium aluminum garnet crystal ($Nd:Y_3Al_5O_{12}$) ("Nd:YAG"), or any other suitable material. In some examples, the solid state gain medium 606 includes a dopant element such as Nd, Yb, Er, Ti, Tm, and/or any other suitable dopant element.

During operation of the laser 600, the pump source 602 causes a population inversion in the solid state gain medium 606 which in turn causes the solid state gain medium 606 to emit laser light having a wavelength the depends on the material of the solid state gain medium 606. For example, if the solid state gain medium 606 is Nd:YAG, the solid state gain medium 606 produces light having a wavelength of 1064 nm.

In the illustrated example, the second reflector 618 is about 100 percent (e.g., 95%, 98%, 99%, 99.9%, etc.) reflective to the light emitted by the solid state gain medium 606 (e.g., 1064 nm for Nd:YAG). The example first reflector 614 has a reflectivity of less than 100 percent (e.g., 80%, 90%, etc.) to the light emitted by the solid state gain medium 606.

In accordance with one or more embodiments, such as the example illustrated in FIGS. 6A-6C, the Q-switch 616 is a passive Q-switch such as, for example, a saturable absorber. A coefficient of thermal expansion of the Q-switch 616 may be substantially equal to a coefficient of thermal expansion of the solid state gain medium 606. In some examples, the Q-switch 616 is implemented using a Cr:YAG crystal. One end of the Q-switch 616 may be non-adhesively bonded (e.g., diffusion bonded, optical contact bonded, etc.) to an end of the solid state gain medium 606. In some such examples, the first reflector 614 is disposed on an opposing end of the Q-switch 616. Some embodiments of the laser do not include the Q-switch 616. As described in greater detail below, the Q-switch 616 prevents the laser from outputting a laser pulse until a population inversion in the solid state gain medium 606 reaches a predetermined level (e.g., a peak level).

During operation, the Q-switch 616 prevents the laser 600 from outputting or transmitting the laser pulse until the population inversion in the solid state gain medium 606 reaches a predetermined level (e.g., a peak level). For example, the Q-switch 616, a saturable absorber, is substantially non-transparent until the population inversion reaches the predetermined level. Once the population inversion reaches the predetermined level, the Q-switch 616 becomes at least partially transparent and the laser pulse passes through the Q-switch 616 and the first reflector 614.

FIG. 6A shows a pulsed laser source 600 that includes an optical parametric oscillator (OPO) that itself includes an external nonlinear crystal 612 that is disposed between reflector 628 and reflector 626. In the illustrated example, the reflector 626, the nonlinear crystal 612, and the reflector 628 may be disposed outside of the reflective cavity formed by the monolithic body 604. Furthermore, the OPO is positioned along a path of the first laser pulse 610 so that the first laser pulse 610 serves as a pump laser pulse that optically pumps the OPO to generate a second set of laser pulses at one or more modified wavelengths, where the modified wavelengths depend on the wavelength of the first laser pulse and one or more properties of the nonlinear crystal 612 of the OPO. As described in more detail below, the one or more properties of the nonlinear crystal may be controlled by a processing system to allow for wide tunability of the modified wavelength.

In the illustrated example, the reflectors 626 and 628 reflect a fundamental wavelength of the first laser pulse 610. As a result, the first laser pulse 610 passes through the reflector 628, and the nonlinear crystal 612 of the OPO converts the first laser pulse 610 to light having a wavelength different than the first laser pulse 610. In the illustrated example, the reflectors 626 and 628 provide an optical resonator for the light produced via the nonlinear crystal 612, and the laser 600 outputs a second laser pulse 624 via the reflector 626 of the OPO.

FIG. 6B illustrates a pulsed laser source 600 that includes an OPO that itself includes nonlinear crystal 612 that is coupled to a heat pump 630 (e.g., a Peltier thermoelectric device) and a heat sink 632 that controls temperature of the nonlinear crystal 612 of the OPO to achieve tunability of a phase matching condition. For example, phase matching may occur for second harmonic generation of light having a wavelength of 1064 nm by adjusting a temperature of a lithium triborate (LBO) crystal to 148° C.

FIG. 6C illustrates a pulsed laser source 600 that includes an OPO that itself includes a nonlinear crystal 612 that has a longitudinal axis 611 that is nonparallel to an optical axis 613 of the monolithic body 604. In the illustrated example, the nonlinear crystal 612 of the OPO is oriented such that the phase matching condition may be tuned by rotating the nonlinear crystal 612.

Figure 6D:
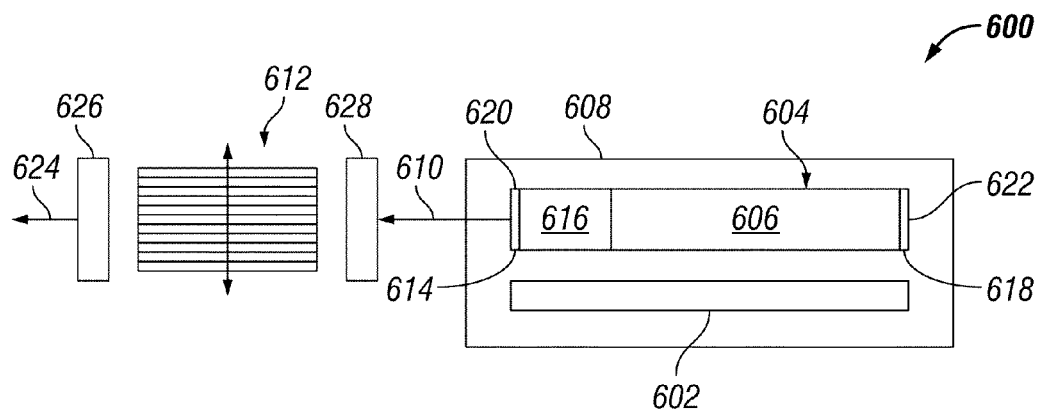

FIG. 6D illustrates a pulsed laser source 600 that includes an OPO that itself includes a nonlinear crystal 612 that is formed having several channels, each channel having a different poling period within the nonlinear crystal 612. Accordingly, when the first laser pulse 610 passes through a particular channel of the nonlinear crystal 612, the crystal will output a laser pulse having a wavelength that depends on the wavelength of the first laser pulse and the poling period of that particular channel. Thus, to alter the output wavelength, the nonlinear crystal 612 may be mechanically translated so that a different channel of the nonlinear crystal 612 having a different poling period is selected for pumping by the first laser pulse 610.

Figure 6E:
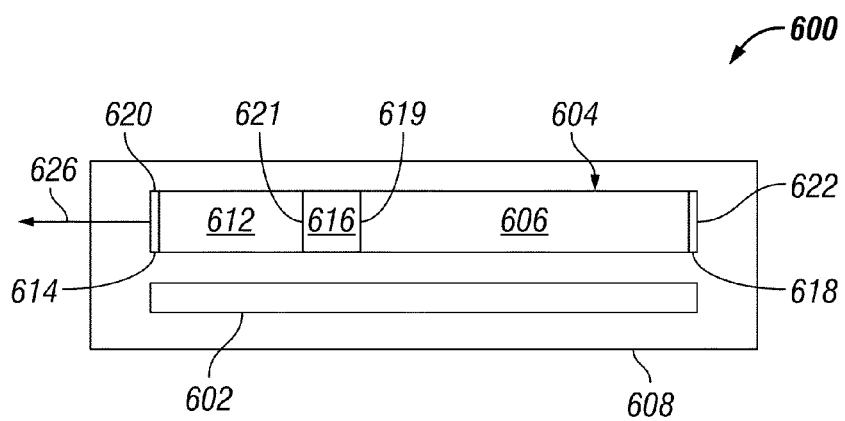

FIG. 6E illustrates a pulsed laser source 600 similar to that described above but further including a nonlinear crystal 612 that is integrated into the monolithic body 604. Accordingly, in this illustrated example, the monolithic body 604 includes a first reflector 614, a nonlinear crystal 612, a Q-switch 616, a solid state gain medium 606, and a second reflector 618. In the illustrated example, a first end 621 of the Q-switch 616 is coupled to the nonlinear crystal 612, and a second end 619 of the Q-switch 616 is coupled to the solid state gain medium 606. In the illustrated example, the first reflector 614 is disposed on a first end 620 of the monolithic body 604 and the second reflector 618 is disposed on a second end 622 of the monolithic body 604. The first reflector 614 is coupled to the nonlinear crystal 612, and the second reflector 618 is coupled to the solid state gain medium 606. In some examples, the first reflector 614 and/or the second reflector 618 are film coatings. In the illustrated example, the first reflector 614 and the second reflector 618 provide an optical resonator, as described above (e.g., in reference to FIGS. 6A-6D).

In this illustrated example, the nonlinear crystal 612 may be composed of Lithium triborate (LBO), potassium titanyl phosphate (KTP), beta-barium borate (BBO), lithium niobate (LN) and/or any other suitable material. In some examples, the nonlinear crystal 612 is a periodically poled material such as, for example, periodically poled lithium niobate (PPLN).

During operation of the laser 600, the pump source 602 causes a population inversion in the solid state gain medium 606 which in turn causes the solid state gain medium 606 to emit laser light having a wavelength the depends on the material of the solid state gain medium 606. The nonlinear crystal 612 converts the light produced via the solid state gain medium 606 to light having a modified wavelength that is different from the wavelength of the light produced via the solid state gain medium 606. For example, if the solid state gain medium 606 is Nd:YAG, the solid state gain medium 606 produces light having a wavelength of 1064 nm, which the nonlinear crystal 612 converts to light having a wavelength of, for example, 532 nm, 354 nm, or 266 nm.

In the illustrated example, one of the first reflector 614 or the second reflector 618 may be anisotropic. The first reflector 614 and the second reflector 618 are about 100 percent (e.g., 95%, 98%, 99%, 99.9%, etc.) reflective to the light emitted by the solid state gain medium 606 (e.g., 1064 nm for Nd:YAG). However, the example second reflector 618 has a reflectivity of about 100 percent (e.g., 95%, 98%, 99%, 99.9%, etc.) to the light produced via the nonlinear crystal 612 while the first reflector 614 has a reflectivity of less than 100 percent (e.g., 80%, 90%, etc.) to the light produced via the nonlinear crystal 612. Thus, the light produced via the solid state gain medium 606 is substantially reflected between the first reflector 614 and the second reflector 618 (i.e., the light is substantially contained in the optical resonator) while the light produced by the nonlinear crystal 612 (i.e., wavelength shifted light) is outputted via the first reflector 614. As a result, the laser 600 outputs a laser pulse 626 having a wavelength of the light produced by the nonlinear crystal 612.

In some examples, the laser source may be a laser source like that shown in FIG. 6E (i.e., one that employs a nonlinear crystal that is integrated into the monolithic body). In other examples, the laser source may employ an external OPO having its own nonlinear crystal and a monolithic body that does not employ a nonlinear crystal, e.g., like the examples illustrated in FIG. 6A-6D. In yet other examples, the laser source may employ a monolithic body that includes a nonlinear crystal and may also employ an external OPO.

In some examples, the wavelength of the output laser pulse may be tuned by changing a phase matching, or quasi-phase matching, condition of the nonlinear crystal used within the OPO. The phase matching condition is highly wavelength dependent and thus, for a given input pulse, the OPO will only efficiently generate output laser pulses at an output wavelength that satisfies the phase matching condition. Thus, a modification of the phase matching condition provides for a modification of the output pulse wavelength for any given input pulse wavelength. For example, as shown in FIG. 6C, the phase matching condition may be changed by altering the angle ϕ between the nonlinear crystal and the direction of the beam 610 entering the OPO.

In addition, the phase matching condition may be modified by altering what is known as the poling period of the nonlinear crystal (in cases where a periodically poled nonlinear crystal is employed). For example, in the illustrative embodiment shown in FIG. 6D, the crystal 612 has several channels, each channel with a different poling period, as described above. A desired phase matching condition may be selected by translating the crystal relative to the output (pump) beam 610.

In another example, the temperature of the nonlinear crystal may be changed in order to change the phase matching condition so as to tune the wavelength of the laser pulses output from the OPO. An example of this type of OPO system is shown in FIG. 6B. In this illustrative embodiment, a temperature control system (not shown) may be used to control a heat pump 630 (e.g., a Peltier thermoelectric device) that is attached to the nonlinear crystal 612. Likewise, in the monolithic design shown in FIG. 6E, a suitable temperature control system (not shown) may be employed to vary the temperature of the nonlinear crystal 612 and thus, to tune the output wavelength.

Figure 7:
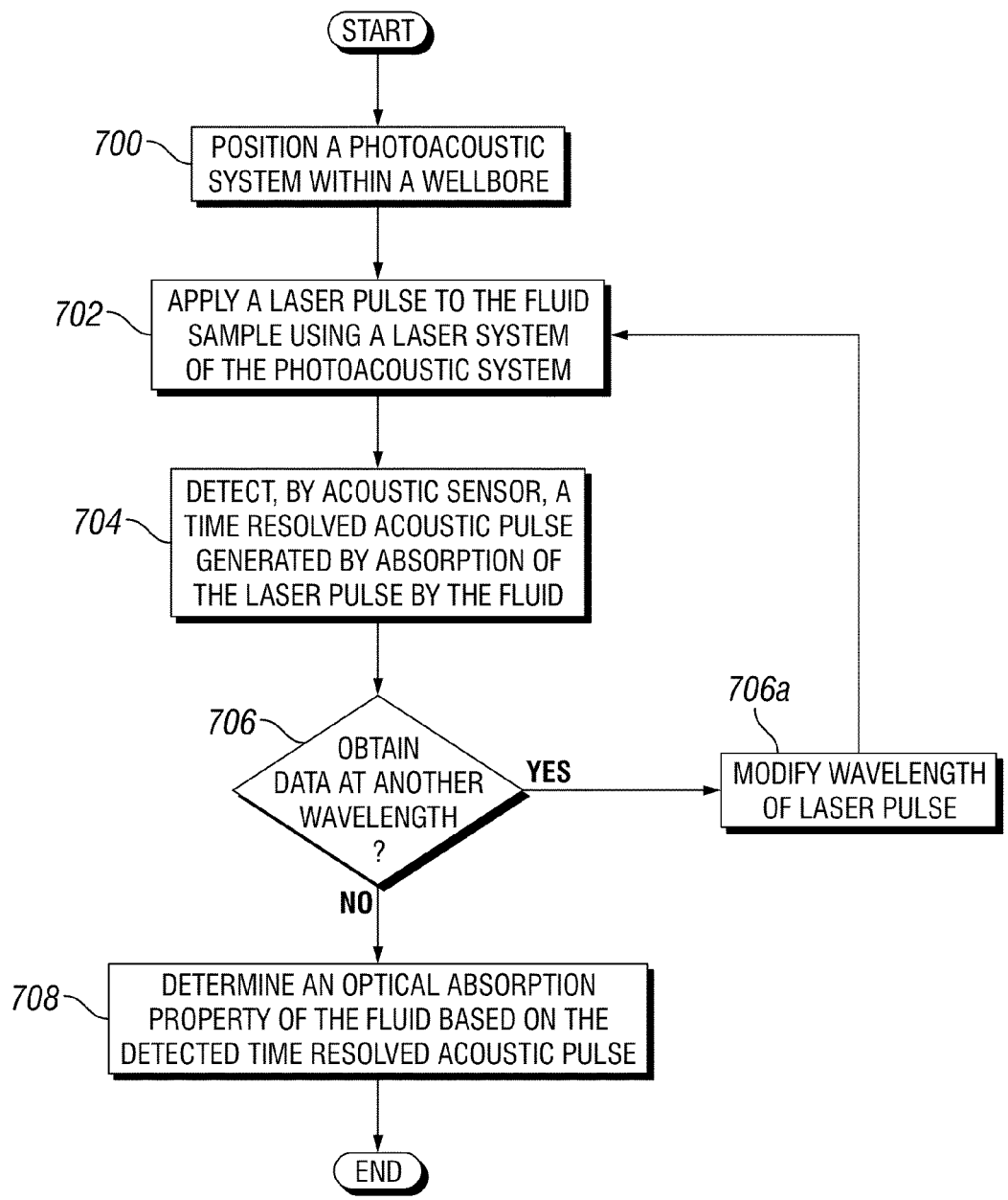
FIG. 7 shows a flow chart for a method for downhole fluid analysis by optical spectroscopy with photoacoustic detection in accordance with one or more embodiments.

FIG. 7 shows a flow chart for a method for downhole fluid analysis by optical spectroscopy with photoacoustic detection in accordance with one or more embodiments. In process 700, a photoacoustic detection system is positioned into a wellbore. In accordance with one or more embodiments, the photoacoustic detection system may be any one of the photoacoustic detections systems described above in reference to FIGS. 3A-3B and FIG. 4. Furthermore, the photoacoustic detection system may be part of a larger wellbore tool (e.g., one of the tools shown and described above in reference to FIGS. 1-2).

In process 702, a laser pulse is applied to the fluid sample using a laser system of the photoacoustic system. The laser pulse may be generated from within a laser cavity of the laser system of the photoacoustic system. For example, in accordance with one or more embodiments, the photoacoustic system may include a laser cavity formed from a single monolithic body that includes a first reflector, a Q-switch, a solid state gain medium, and a second reflector. An example of such a laser cavity formed from a monolithic body is described above in reference to FIGS. 6A-6C. In accordance with one or more embodiments, the Q-switch may be used to modulate the quality factor of the solid state gain medium and thereby generate the laser pulses directly from the gain medium without a need for external chopper wheels or the like. Furthermore, the Q-switched solid state source allows for laser pulses having short durations (e.g., having durations in the range of 1-100 ns). In accordance with one or more embodiments, the Q-switch may be a passive Q-switch in the form of a saturable absorber that may be non-adhesively bonded to the end of the solid state gain medium (e.g., by way of diffusion bonding, optical contact bonding, etc.). In some examples, the generated laser pulses are directed by an optical system to a window in the photoacoustic system and enter the fluid under test. In accordance with one or more embodiments, the laser pulses are absorbed by the fluid thereby inducing an acoustic pulse in the fluid as described in further detail above in reference to FIGS. 5A-5B.

In process 704, the acoustic pulse is detected by an acoustic sensor (e.g., a piezoelectric transducer or the like). In accordance with one or more embodiments, the acoustic sensor detects the fluid pressure as a function of time thereby generating what is referred to herein as time-resolved acoustic pulse data. An example of time resolved acoustic pulse data is shown in FIG. 5B and is described above in the accompanying description.

In process 706, a decision is made whether or not to conduct another photoacoustic measurement at a different laser wavelength (e.g., in a case where a photoacoustic spectrum is desired to be measured). If the system determines that another data point is indeed required, the method proceeds to step 706a, where the laser wavelength is modified before another photoacoustic measurement is conducted. For example, in one example, computer readable instructions may be stored on the memory of a processing system of the tool. These stored instructions may indicate that a single measurement is to be obtained or a series of measurements at a predetermined series of wavelengths is to be obtained. Furthermore, when the instructions executed by a processor of the processing system, the processing system generates a control signal that causes the laser system to alter the laser pulse wavelength by modifying a control signal that is applied to a nonlinear crystal of an OPO (e.g., as the OPO described above in reference to FIGS. 6A-6E). For example, the wavelength of the output pulse of the pulsed laser may be scanned by tuning the phase matching condition of the pulsed laser by varying the temperature, alignment angle, or displacement of the nonlinear crystal of the pulsed laser as described above in reference to FIGS. 6A-6E. In some embodiments, the processor may determine that a measured signal to noise ratio (or some other criteria) is too low and then direct the system to acquire additional data points at the same or nearby wavelengths as those already acquired.

When the data is collected and no additional data points are desired, the method proceeds to process 708 where, for each data point, an optical absorption property is determined based on the detected time resolved acoustic pulse. For example, for each pulse, the rising edge of the time resolved acoustic pulse data is fit to a rising exponential function and the exponential time constant is extracted from the fit, e.g., as described above in reference to FIG. 5B. As described above, the extracted time constant is directly proportional to the absorption coefficient of the fluid under test. This analysis process may proceed for a single point only or may proceed for multiple data points having several different wavelengths, thereby providing information related to the absorption properties of the fluid as a function of laser pulse wavelength. In other words, an optical absorption spectrum may be determined from the time resolved photoacoustic data. Further details of this analysis are described above in reference to FIGS. 5A-5B.

In the illustrative examples described above, the use of an OPO allows for the wavelength of the laser pulse to be tuned over a wide range of wavelengths. For a periodically poled lithium niobate crystal the wavelength may be tuned over a range of 1410 nm to 4335 nm. In another example, a doubled Nd:YAG system may allow for tuning over a range of 355 nm to 4500 nm. Other OPO crystals, such as chalcogenide (e.g., gallium selenide (Gase)), would allow for tuning at far infrared wavelengths (e.g., wavelengths at 1 to 20 microns and greater). Accordingly, the tunable pulsed laser system coupled with a photoacoustic detection system allows for the spectroscopic analysis of fluids over a wide range of wavelengths. Furthermore, the use of photoacoustic detection allows for spectroscopic measurements to be made in fluids that have strong scattering properties (e.g., in fluids where traditional absorption spectroscopy would not be feasible). Likewise, the use of photoacoustic detection in combination with the tunable laser source allows for spectroscopic measurements of high optical density (OD) fluids (e.g., fluids having an absorption coefficient as high as about 15-20 $cm^{-1}$ and in some cases up to 1000 $cm^{-1}$ or greater). In various embodiments, spectroscopic measurements are made on fluids where less than 37% (1/e) of the incident light is transmitted through the fluid due to optical absorption or scattering. Furthermore, in some embodiments, less than 10% of the incident light is transmitted through the fluid due to optical absorption or scattering.

In accordance with one or more embodiments, the wide tunability of the laser source allows for the system to perform optical spectroscopy in any number of different fluids. For example, FIGS. 8A-8C show examples of absorption spectra of several different types of fluids that may be characterized using the system in accordance with one or more embodiments. FIG. 8A shows absorption spectra for water, medium-weight oil, and $CO_2$, while FIG. 8B shows absorption spectra for condensate, volatile oil, black oil, heavy oil and water. FIG. 8C shows absorption spectra for a number of different asphaltenes, as described in further detail in, for example, Ruiz-Morales et al., Polycyclic Aromatic Hydrocarbons of Asphaltenes Analyzed by Molecular Orbital Calculations with Optical Spectroscopy, Energy and Fuels, 21, 256-265 (2007). As used herein, the term heavy oil refers to oils having an asphaltene content greater than about 5% by weight (5 wt. %.). As used herein, the term black oil refers to an oil having an asphaltene content of less than about 5 wt. % and also having more asphaltenes than a volatile oil or condensate. Furthermore, as referred to herein, the term asphaltene is defined to be the component of oil that is soluble in toluene but not soluble in an aliphatic solvent, such as pentane.

In accordance with one or more embodiments, the composition of the fluid under test may be obtained by first obtaining an absorption spectrum of the fluid and then fitting a spectral model as is known in the art (e.g., by way of a non-linear least squares fit or the like). For example, the measured data may be fit to a model that includes a linear combination of one or more component spectra (e.g., the spectra shown in FIGS. 8A-8C). The fitting coefficients of the linear combination are proportional to the abundances of the respective components within the fluid under test and thus, the abundances may be determined using the fitting procedure in combination with an appropriate calibration and normalization procedure.

Furthermore, due to insensitivity to scattering, the systems and methods disclosed herein may be used to perform spectroscopy on oils that form emulsions with water. As used herein an emulsion refers to a fluid system liquid droplets are dispersed within another liquid (e.g., oil droplets dispersed in water or water droplets dispersed in oil). As used herein a significant scatterer is one with more than 1 OD of scattering, and a significant absorber is one with more than 1 OD of absorption.

The systems and methods disclosed herein generally relate to methods and systems for optical spectroscopy with photoacoustic (PA) detection for the characterization of unknown fluid samples (e.g., unknown unconventional hydrocarbon fluid samples). It will be appreciated that the same systems and methods may be used for performing subsurface analysis in fields such as oilfield, mining, water retrieval, or in any field where fluid sample characterization is desired. Furthermore, in accordance with one or more embodiments, the system may be deployed as a stand-alone analytical instrument (e.g., as a lab-based analytical instrument or as ruggedized unit for field work), or as part of a wellbore tool for in situ formation characterization (e.g., as part of a wireline tool, a logging while drilling ("LWD") tool, or a measurement while drilling ("MWD") tool). The systems and methods disclosed herein are not limited to the above-mentioned applications and these applications are included herein merely as a subset of examples.

Some of the processes described herein, such as (1) receiving an electric signal from an acoustic sensor that is representative of acoustic pulses, (2) determining an optical absorption property of a fluid sample using the electric signal, (3) fitting a pressure rise of a time-resolved acoustic pulse to an exponential function, (4) determining presence of a component within the fluid sample using the optical absorption property, (5) determining a quantity of a component within the fluid sample using the optical absorption property, and (6) controlling operation and tuning of the laser system, can be performed by a processing system.

In one embodiment, the processing system is located at the well site as part of surface equipment (e.g., the electronics and processing 126 in FIG. 1). The processing system communicates with the wellbore tool via, for example, an armored cable or mud pulse telemetry. In a second embodiment, the processing system is incorporated into the wellbore tool. In another embodiment, the surface equipment and wellbore tool each include processing systems. In yet another embodiment, however, the processing system is located remote from the well site at an office building or a laboratory to support the lab-based analytical instrument described above.

The term "processing system" should not be construed to limit the embodiments disclosed herein to any particular device type or system. In one embodiment, the processing system includes a computer system. The computer system may be a laptop computer, a desktop computer, or a mainframe computer. The computer system may include a graphical user interface (GUI) so that a user can interact with the computer system. The computer system may also include a computer processor (e.g., a microprocessor, microcontroller, digital signal processor, or general purpose computer) for executing any of the methods and processes described above (e.g., processes 1-6 above and processes 700-708 in FIG. 7).

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. This memory may be used to store, for example, data from the wellbore tool.

Some of the methods and processes (e.g., processes 1-6 above and processes 700-708 in FIG. 7) can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Additionally or alternatively, the processing system may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

Although several example embodiments have been described in detail above, those skilled in the art will readily appreciate that many modifications are possible in the example embodiments without materially departing from the scope of this disclosure. Accordingly, all such modifications are intended to be included within the scope of this disclosure.

What is claimed is:

1. A wellbore tool comprising: a photoacoustic spectroscopy system for analyzing a fluid sample, the system comprising: a laser system that is configured to generate laser pulses; a window disposed between the fluid sample and the laser system and configured to transmit the laser pulses to the fluid sample; an acoustic sensor configured to receive acoustic pulses that are generated in response to absorption of the laser pulses by the fluid sample; and a processing system configured to determine an optical absorption property of the fluid sample by (a) fitting an exponential function to a pressure rise of an acoustic pulse or (b) measuring a slope of a semi-log plot of a pressure rise of the acoustic pulse.

2. The wellbore tool of claim 1, wherein the window is disposed on an exterior wall of a wellbore tool and the fluid sample is disposed outside the wellbore tool.

3. The wellbore tool of claim 2, wherein the acoustic sensor is disposed on the window.

4. The wellbore tool of claim 1, wherein the window is disposed along a flow line of the wellbore tool and the fluid sample is disposed within the flow line.

5. The wellbore tool of claim 4, the acoustic sensor is disposed along the flow line of the wellbore tool.

6. The wellbore tool of claim 1, wherein the laser system comprises a laser cavity with a monolithic body having a first end and a second end, the monolithic body comprising a first reflector disposed on the first end, a second reflector disposed on the second end, a solid state gain medium and a Q-switch, wherein the solid state gain medium and the Q-switch are disposed between the first reflector and the second reflector of the monolithic cavity.

7. The wellbore tool of claim 6, further comprising a pump source, wherein the pump source is configured to cause a population inversion in the solid state gain medium to cause the monolithic body to generate laser pulses.

8. The wellbore tool of claim 1, wherein the laser system comprises:
   a pump laser configured to generate a pulse of pump laser light; and
   an optical parametric oscillator configured to generate the laser pulses, wherein a wavelength of the laser pulses depends on a wavelength of the pulse of pump laser light and a control signal applied to a nonlinear crystal of the optical parametric oscillator.

9. The wellbore tool of claim 1, further comprising a processing system configured to (i) receive an electric signal from the acoustic sensor representative of the acoustic pulses and (ii) determine a property of the fluid sample using the electric signal.

10. A method for analyzing a fluid sample, the method comprising:
   positioning a photoacoustic system within a wellbore, wherein the photoacoustic system comprises a pulsed laser system and an acoustic sensor;
   applying a laser pulse to the fluid sample using the pulsed laser system;
   detecting, by the acoustic sensor, a time-resolved acoustic pulse generated by absorption of the laser pulse by the fluid sample; and
   determining an optical absorption property of the fluid sample by (a) fitting an exponential function to a pressure rise of the time-resolved acoustic pulse or (b) measuring a slope of a semi-log plot of a pressure rise of the time-resolved acoustic pulse.

11. The method of claim 10, further comprising:
determining presence of at least one component within the fluid sample using the optical absorption property.

12. The method of claim 10, further comprising:
determining a quantity of at least one component within the fluid sample using the optical absorption property.

13. The method of claim 12, wherein the at least one component comprises asphaltenes.

14. The method of claim 10, wherein (i) applying the laser pulse to the fluid sample comprises applying a plurality of laser pulses using a plurality of different wavelengths and (ii) detecting the time-resolved acoustic pulse comprises detecting time-resolved acoustic pulses for each of the plurality of different wavelengths.

15. The method of claim 14, wherein determining the property of the fluid sample comprises determining a plurality of optical absorption properties for each of the plurality of wavelengths.

16. The method of claim 15, further comprising:
determining at least one component within the fluid sample using the plurality of optical absorption properties.

17. The method of claim 10, wherein applying the laser pulse comprises modulating a quality factor of a gain medium within the laser system using a passive Q-switch.

18. The method of claim 14, wherein applying a plurality of pulses using a plurality of different wavelengths comprises varying at least one of a nonlinear crystal temperature and a nonlinear crystal orientation.

19. The method of claim 14, wherein a range of wavelengths of the plurality of wavelengths is a range from 355 nm to 4500 nm.

20. A method for analyzing a fluid sample, the method comprising:
applying a laser pulse to the fluid sample using a laser system, wherein less than 37% of light from the laser pulse is transmitted through the fluid sample;
detecting a time-resolved acoustic pulse generated by absorption of the laser pulse by the fluid sample using an acoustic sensor; and
determining an optical absorption property of the fluid sample by (a) fitting an exponential function to a pressure rise of the time-resolved acoustic pulse or (b) measuring a slope of a semi-log plot of a pressure rise of the time-resolved acoustic pulse.

21. The method of claim 20, wherein the fluid sample comprises a heavy oil.

22. The method of claim 20, wherein the fluid sample comprises an emulsion.

23. The method of claim 20, wherein the fluid sample comprises asphaltenes.

\* \* \* \* \*